United States Patent
Sovak et al.

[11] Patent Number: 6,123,928
[45] Date of Patent: Sep. 26, 2000

[54] SUNBLOCKING POLYMERS AND THEIR NOVEL FORMULATIONS

[75] Inventors: Milos Sovak, La Jolla; Ronald C. Terry; James G. Douglass, III, both of San Diego; Farid Bakir, Del Mar; Jason Brown, Encinitas; Peter Cugley, San Diego, all of Calif.

[73] Assignee: Biophysica, Inc., La Jolla, Calif.

[21] Appl. No.: 09/119,836

[22] Filed: Jul. 21, 1998

Related U.S. Application Data

[63] Continuation-in-part of application No. 09/046,945, Mar. 23, 1998, abandoned, which is a continuation-in-part of application No. 08/490,316, Jun. 14, 1995, Pat. No. 5,741,924, which is a continuation-in-part of application No. 08/164,881, Dec. 9, 1993, Pat. No. 5,487,885, which is a continuation-in-part of application No. 07/994,426, Dec. 21, 1992, abandoned.

[51] Int. Cl.[7] ............... A61K 7/42; A61K 7/44; A61K 7/00; A61K 31/78

[52] U.S. Cl. ............ 424/59; 424/60; 424/78.02; 424/400; 424/401; 526/328; 526/328.5; 526/329.2; 526/329.5; 526/304; 526/307; 526/307.7

[58] Field of Search ............ 424/59, 60, 78.02, 424/400, 401; 526/328, 328.5, 329.2, 329.5, 304, 307, 307.7

[56] References Cited

U.S. PATENT DOCUMENTS

| | | | |
|---|---|---|---|
| 2,764,613 | 9/1956 | Grunwald | 564/171 |
| 3,980,617 | 9/1976 | Jacquet et al. | 424/59 |
| 4,003,617 | 1/1977 | Jacquet et al. | |
| 4,233,430 | 11/1980 | Jacquet et al. | |
| 4,525,061 | 6/1985 | Cho et al. | |
| 4,661,616 | 4/1987 | Hill | 560/55 |
| 5,041,282 | 8/1991 | Sabatelli et al. | |
| 5,063,048 | 11/1991 | Saitoh et al. | |
| 5,134,223 | 7/1992 | Langer et al. | |
| 5,243,021 | 9/1993 | Langer et al. | |
| 5,250,652 | 10/1993 | Langer et al. | |
| 5,487,885 | 1/1996 | Sovak et al. | 424/59 |

FOREIGN PATENT DOCUMENTS

| | | | |
|---|---|---|---|
| 37 00 531 A1 | 7/1987 | Germany. | |
| 888664 | 1/1962 | United Kingdom | 564/194 |
| WO 93/22413 | 11/1993 | WIPO. | |

OTHER PUBLICATIONS

Dromgoole et al (1990) "Sunscreening Agent Intolerance, Contact and Photocontact Sensitization and Contact Urticaria" *J. Amer. Derm.* 22: 1068–1078.
Japanese Geon Ltd. (1968) C.A. 68:3801.
Ker et al (1989) C.A. 111:140208.
Lowe (1990) Photoprotection *Sem. Derm.* 9:78–83.
Shah et al (1990) C.A. 113:217980.
Shairishi et al (1990) C.A. 113:84646.
Tirrell et al (1979) C.A. 91: 145926.

*Primary Examiner*—Shelley A. Dodson
*Attorney, Agent, or Firm*—Bertram I. Rowland; Rae-Venter Law Group, P.C.

[57] ABSTRACT

Novel polymeric biologically inert compositions and their intermediates, as well as sunscreen formulations comprising them and making them invisible, are provided for broad range protection from ultraviolet radiation. Acryl polymers comprising at least two different ultraviolet absorbing moieties having different light absorbing ranges are employed in conjunction with other monomers to provide sunscreen polymers as microparticles. The polymer microparticles, once imbibed with carrier compounds, change the refractive index, thus providing invisible sunscreen formulations which offer enhanced protection without adverse physiological effects.

22 Claims, No Drawings

SUNBLOCKING POLYMERS AND THEIR NOVEL FORMULATIONS

CROSS-REFERENCE TO RELATED APPLICATIONS

This application is a continuation-in-part of application Ser. No. 09/046,945, filed Mar. 23, 1998 now abandoned, which is a continuation-in-part of application Ser. No. 08/490,316, filed Jun. 14, 1995 now U.S. Pat. No. 5,741,924, which is a continuation-in-part of application Ser. No. 08/164,881, filed Dec. 9, 1993 now U.S. Pat. No. 5,487,885, which is a continuation-in-part of application Ser. No. 07/994,426, filed Dec. 21, 1992, now abandoned.

INTRODUCTION

1. Technical Field

The field of this invention is novel sunblock(s) and their formulations for use in dermatological applications.

2. Background

The role of ultraviolet radiation in skin aging and in the development of skin cancer is being increasingly recognized. For protection of the skin, the state of art utilizes various UV-absorbing chemical compounds, primarily singular (monomeric) aromatic compounds and/or reflecting pigments, i.e. metal oxides, which are formulated into creams and lotions. Many of such cream and lotion formulations are presently available and are widely used.

Unfortunately, however, there are many disadvantages to the known aromatic UV blocking formulations, wherein one of such disadvantages is their lack of biological tolerance. Due to their chemotoxicity and allergenicity, as well as other side-effects, the various UV-absorbing additives, in spite of being limited, often exercise their adverse potential. As these UV-blocking compounds penetrate into the skin where they convert the absorbed UV radiation into heat, which in turn dilates the vessels, a sensation that is perceived as unpleasant. The reflecting inorganic pigments, such as zinc or titanium oxides, are strongly and adversely visible on the skin, even if micronized, nanomized and/or tinted. In this regard, while nanomized oxides tend to be less visible than the other oxides employed, they tend to penetrate into the tissue and cause inflammatory reactions.

An ideal sun radiation blocking formulation should be invisible on the surface of the skin and should be non-absorbable to be completely biologically inert. The UV blocking agent of the formulation should cover the entire UV range of atmospheric radiation. Desirably, the blocking agent should also absorb, reflect and diffract the infrared radiation known to potentiate the carcinogenic and inflammatory effect of ultraviolet light. There is, therefore, substantial interest in developing novel sun blocking formulations which approximate these ideals.

Relevant Literature

Dromgoole and Maibach, *J. Am. Academy of Dermatology*, Mosby Year Book, 1990, Chapter 8, describe contact sensitization and photocontact sensitization of sunscreening agents. Harber, et al., in *Photosensitivity Diseases, Principles of Diagnosis and Treatment*, B. Decker, Toronto, 1989, Chapter 10, page 141, describe intrinsic and extrinsic photoprotection against UV-B and UV-A radiation. Lowe, ibid, Chapter 11, page 161 describes the screening of various sun protection compositions.

In Japanese application No. 5-125118, filed Nov. 2, 1991, a para-amino benzoyl substituted polyacrylic acid as a sun blocking composition is reported, where a para-aminobenzoyl group is joined to the polyacrylic acid by a variety of linking groups. See also CA102:221311d which describes para-aminobenzoyl substituted acrylic polymers.

SUMMARY OF THE INVENTION

UV absorbing microparticulate, biologically inert acrylic polymers formulated to be substantially imperceptible as a thin layer on the skin are provided wherein the polymers have a plurality of UV absorbing moieties that substantially cover the wave-length range of light (sunlight) which penetrates to the earth's surface and is undesirable for the health of the subject. The sun blocking polymers are formulated in particular ways for efficacy, transparency and stability in aqueous milieu. Preferably, the polymers may be formulated in combination with a tocopherol or one or more of its functional analogs or derivatives or in one or more of a variety of known vegetable, mineral or silicone oils, and the like, with the addition of substantially or strictly non-toxic organic and/or inorganic additives. The formulations provide for safe protection against the deleterious effects of UV radiation on the skin and surprisingly provide for sunscreens that are biologically inert and substantially unobsevable during their residence on the skin.

DESCRIPTION OF SPECIFIC EMBODIMENTS

Novel sun blocking polymeric compositions and their formulations are provided wherein the polymeric compositions comprise at least two different UV absorbing moieties and a moiety other than a UV absorbing moiety on the acrylic backbone. The compositions find use as sun blocking agents in a variety of contexts. The polymers may be prepared by combining the individual monomers under addition polymerizing conditions, which may involve precipitation or emulsification in appropriate amounts, taking into consideration the differential rates of incorporation of the different monomers, whereby a product is obtained having an effective proportion of monomers which absorb UV light in the wave length range to which skin is deleteriously exposed on earth.

Normally, in the polymers employed in the formulations of the present invention, UV absorbers of at least UV-A and UV-B will be present, wherein there could also optionally be an absorber for UV-C. In addition, there will be at least one other monomer which will be an acrylic acid (includes α-substitutents, e.g. methyl), particularly a derivatized acrylic acid, more particularly derivatized carboxyl groups, such as esters and amides, where the group bonded to the carboxyl may be hydrophilic or hydrophobic, the latter having one or more oxy groups, usually not more than about 6 oxy groups, hydroxyl and ether. For the most part, the number ratio of total UV absorbers to other monomer(s) in the polymer will be in the range of about 0.1–10:1, usually 0.5–5:1, more usually 1–5:1. Of the UV absorbers present in the polymer, there will generally be about 30–98 number percent of the UV-B absorber, more usually from about 50 to 95 number %, at least 2 number percent of the UV-A absorber, usually at least about 5 number %, and optionally the remainder being the UV-C absorber, if present. Depending upon the individual monomers, the ratio of the UV absorbing monomers to the other monomers in the polymerization reaction mixture, the absence or presence of a cross-linking agent, and the like, the molecular weight may vary widely, where the composition of individual molecules may vary as the polymerization proceeds. To obtain high molecular weight polymer, it will be desirable to use small amounts of a cross-linking agent, generally from about 0.5–10 mole percent, more usually from about 1–3 mole percent of total monomer.

To be biologically inert, the UV-absorbing polymeric molecules will often be completely insoluble in water, but desirably will absorb and swell in non-aqueous media to be transparent, and remain transparent as a thin film in the presence of water. Desirably, a carrier composition for the polymer shall comprise a tocopherol and/or one or more of its analogs or derivatives having Vitamin E activity, or various vegetable, mineral or silicone oils. The tocopherol derivatives will usually be not more than about 60 carbon atoms, usually not more than about 40 carbon atoms, particularly not more than about 35 carbon atoms, usually being esters. Further, various additives such as small amounts of a metal oxide and/or ascorbate may be added for increased protection, while still maintaining transparency and stability of the composition.

The UV-absorbing monomers will desirably have high extinction coefficients, at least about 20,000, preferably in excess of about 25,000.

The UV-A absorbers will, for the most part, be benzophenones, bis-benzoylmethane or benzotriazole compounds, substituted with appropriate substituents for providing the desired light absorption characteristics, other desirable properties, as well as for linking to the acryl group. Preferred UV-A absorbers have a $\lambda_{max}$ in excess of 340 nm. In addition, the UV-A absorbers will usually have enhanced stability in sunlight, particularly when incorporated in the subject polymeric compositions. For the most part, the UV-A absorbers of the subject composition will have one of the following formuli:

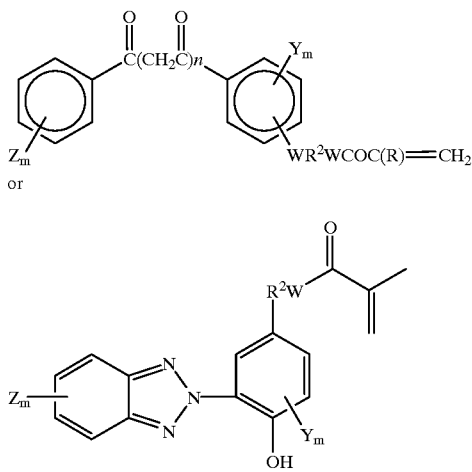

wherein:
n is 0 or 1;
m is 0, 1, 2 or 3;
R is H, alkyl of from 1 to 3, usually 1 to 2, carbon atoms, which may be substituted with a functional group having from 1 to 2 heteroatoms, which are N or O;
$R^2$ is a bond, with the proviso that when $R^2$ is a bond or only one carbon atom, only one W is present or is a divalent hydrocarbylene group or substituted hydrocarbylene group, having up to 2, usually up to 1 substituent, where the substituent will be composed of oxygen, nitrogen, phosphorus, carbon and hydrogen, having from 1 to 3 heteroatoms, usually 1 to 2 heteroatoms, where the heteroatom may be in the chain, and from 0 to 6, usually 0 to 4 carbon atoms, which group may be aliphatic, alicyclic or aromatic, generally of from 1–8, usually of from 2–8, more usually of from 2–6 carbon atoms, particularly phenylene or alkylene;

Z is oxy, particularly hydroxy or alkoxy of from 1–6, more usually 1–3 carbon atoms, amino having from 0–2 alkyl substituents having a total of from about 1–12, more usually from about 1–6 carbon atoms, alkyl of from 1 to 5 carbon atoms, usually 1 to 2 carbon atoms, or hydrogen;

Z will preferably be at the para position to the carbonyl group;

Y is non-oxo carbonyl, which includes the carboxylic acid, carboxyl ester, where the ester will normally have an alkyl group of from 1–6, usually from 1–3 carbon atoms, or carboxamide, where the amino may be substituted or unsubstituted, where the substituted amino will have from 1–2 alkyl substituents with a total of from 1–12 carbon atoms, usually of from 1–6 carbon atoms;

Y is preferably at the ortho position in relation to the carbonyl;

W is oxy (—O—) or amino (—N($R^1$)), where $R^1$ is hydrogen or alkyl of from 1–6, usually 1–3 carbon atoms, where W is preferably oxy, when n is 1;

there being from 0–2, usually 0–1 Y.

Where the same symbol may be present a plurality of times, each of the incidences may be the same or different.

In addition, the rings may be substituted with from 0–3, usually 0–2 alkyl groups of from 1–6, more usually 1–3 carbon atoms, at available positions on the rings.

For the UV-B absorbers, the compounds for the most part will be benzoyloxy derivatives, particularly substituted benzoyloxy derivatives, more particularly para-amino substituted benzoyloxy derivatives and derivatives of cinnamic acid. For the most part, these compounds will come within one of the following formulae:

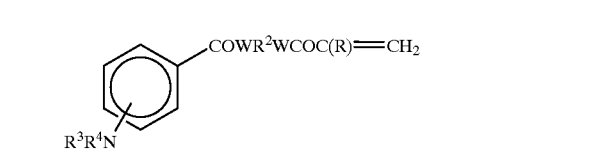

wherein:
$R^3$ and $R^4$ are hydrogen or alkyl up to 6 carbon atoms, usually 1–3 carbon atoms, preferably methyl, and are the same or different; and
W, R and $R^2$ are as defined previously; or

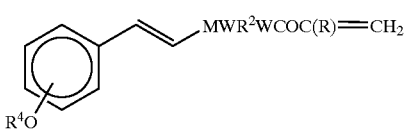

wherein:
M is carbonyl or methylene and W, R, $R^2$ and $R^4$ are as defined above.

The UV-C absorbing compound will be an oxybenzoyl derivative bonded to an acryl group through a divalent bridging moiety. For the most part, the UV-C absorbing group will have the following formula:

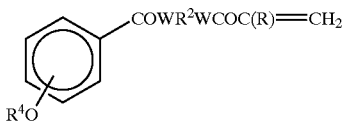

wherein:

$R^4$ is hydrogen or alkyl of from 1–6, usually 1–3 carbon atoms, preferably methyl, and the remaining symbols have been defined previously.

The remaining monomers may be substituted or unsubstituted will usually have at least one organic substituent, which may be the same or different as to the individual monomers, there usually being a total of not more than about 4 different groups, the substituent being unsubstituted or more usually having at least one polar group, particularly an oxy group on a side chain. For the most part, these compounds will be of relatively low molecular weight, generally being under about 800 Dal, more usually being under about 400 Dal. They will normally be aliphatic, particularly saturated aliphatic, i.e. alkyl of from 1 to 6, usually 2 to 6 carbon atoms, have at least 1 oxy group and may have up to 4 oxy groups, generally having from 1–3 oxy groups, more usually having from 1–3 hydroxy groups. For the most part, these compounds will have the following formula:

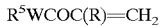

wherein:

$R^5$ is hydrogen, a counterion, e.g. alkali metal, ammonium, etc., an aliphatic group of from 1–8 carbon atoms, usually 1–6 carbon atoms, particularly alkyl, having from 1–5, usually 1–3 oxy groups, more usually hydroxy groups;

the remaining symbols have been defined previously.

In some instances polymers may be prepared which have a single UV absorber class, particularly, UV-A. For this purpose, any of the UV-A absorbers may be used, preferably the dibenzoylmethylene UV-A absorbers. These absorbers may be polymerized with one of more acrylic acid monomers, particularly esters, more particularly oxy substituted esters, having from about 1 to 3, usually 1 to 2, oxy groups and of from 2 to 8, usually 2 to 6, carbon atoms. The mole ratio of UV absorbers to non-UV absorbers (the acrylic acid monomers) will be in the same range as provided for having two UV absorbers. These polymers may be used as sunscreens by themselves or may be combined with other polymeric compositions, particularly polymeric compositions according to the subject invention, or with non-polymerics Monomers of interest are acrylic acid, methacrylic acid, and their hydrophilic and hydrophobic amides or esters, such as hydroxyethyl and hydroxypropyl amides and esters, and ethyl, propyl, butyl, pentyl and hexyl amides and esters.

In the above formulas, the oxy or amino substituent may be substituted with a 2-nitrovinyl group to provide the desired radiation absorbing characteristics.

Compounds of interest include building blocks of p-aminobenzoic acid, p-methoxybenzoic acid, o-hydroxybenzoyl, p-dimethylaminobenzoic acid, p-aminobenzoyl, acetoxyhydroquinone, phenylenediamine, etc.

Compounds of interest include N,N-diallylamino, N'-acryl or methacryl phenylenediamine, p-acryloxy or methacryloxybenzoate alkyl ester, N-alkyl m-acrylamido- or methacrylamidobenzoate alkyl ester, p-benzoyloxyacrylanilide or -methacrylanilide, p-acrylamido or -methacrylamidobenzoate methyl ester, o-acryloxy or -methacryloxy-dibenzoylmethane, p-acryloxy or -methacrylamidodibenzoylmethane, 4-acetoxy-1-acryloxy or -methacryloxybenzene, 2,4-dimethylamino-1-acryloxy or -methacryloxybenzene, N,N-bis-(3-acryloxy or -methacryloxyphenyl) methylamine, m-acryloxy or -methacryloxy-dibenzoylmethane, p,p'-diacryloxy or -methacryloxydibenzoylmethane, m,m'-diacryloxy or -methacryloxydibenzoylmethane, m,p'-diacryloxy or -methacryloxydibenzoylmethane, m- or p-acryloxy or -methacryloxy-2-nitrostyrene, 4-acryloxy or -methacryloxy-4'-(1"-(2"-nitrovinyl))dibenzoyl-methane, 2-(2'-hydroxy-5'-[2"-methacryloxyethyl]phenyl)-2H-benzotriazole, and the like, where alkyl is 1–3, usually 1 carbon atom.

Any convenient cross-linking agent may be employed, which will usually be a bis-acryl, -methacryl or erythritol where the lining group may be any convenient group. Thus, the linking group may be methylene, amino, particularly substituted amino, 1,2-dioxyethylene, oxyamino, diaminoethylene, 1,4-dioxybutylene, dialkylenephosphate ester, α,α'-xylylenediamino, etc.

Polymers of particular interest comprise from about 20 to 60, usually 25 to 60 mol % acrylic acid. In addition, the mol ratio of the UV-B to UV-A monomers will generally be in the range of 50:50 to 98:2, preferably 60:40 to 95:5. Polymers coming within this composition tend to readily form small particles without grinding, where the particles may be directly used in the sunscreen formulation, or ground first.

The subject monomers may be prepared from commercially available intermediates in accordance with known ways. A substantial number of starting monomers are provided in the accompanying working exemplification, which may serve as models for the production of a variety of monomers coming within the subject invention. In addition, the polymerization may be carried out in accordance with conventional ways, using free radical catalysts at relatively mild temperatures and a solvent system to achieve emulsion or suspension in situ. Thus, peroxy compounds, azo compounds, ultraviolet light, or the like may be used as a source of polymerization initiation at temperatures in the range of about 10 to 70° C. for the polymerization. Usually, the polymerization will take place in the absence of oxygen, preferably under an inert atmosphere. The time for the polymerization will usually be at least an hour, usually at least 2 hours, and may extend to 24 hours or more, depending upon the conditions for the polymerization. A solvent may be used, e.g. an alkanol, particularly methanol, or a hydrocarbon, such as toluene, or the like, in which the various monomers are soluble. Generally, the solvent may be present in from about 0.2–10:1 weight ratio to the monomer charge. In the preparation of hydrophobic particulate polymers, the acrylic acid derivative may serve as a solvent, and an inhomogeneous system containing water may be employed After completion of the polymerization, the polymer may be isolated in accordance with conventional ways, and purified as appropriate.

The product as formed will generally be small particles in the range of about 1–5μ. While these particles may be used in the sunscreen formulation, normally they will be further ground so that at least about 90 weight % of the particulate product has a diameter of less than about 1μ, where 80 weight % or more may be less than about 0.75μ in diameter.

The subject polymers may be readily formulated with appropriate vehicles to provide the desired composition. For dermatological use, the subject polymers are formulated in creams, lotions, salves, and the like, to produce an adherent smooth invisible film and to partially diffract the UV and infrared radiation. A wide variety of emollients are taught in the literature and include silicone, mineral and vegetable oils, petrolatum (purified petroleum hydrocarbon greases), and the like. Depending upon the nature of the polymeric product, the polymeric product may be milled, ground or otherwise reduced in particle size in the presence of an oil, conveniently physiologically tocopherol, e.g. α-tocopherol, and/or its derivatives, e.g. esters, or a hydrocarbon oil. Of interest is the use of additives, such as other microparticles of other polymers, such as partially hydrolyzed polyacrylamides or ultrafine titanium or zinc oxides or ascorbic acid and its derivatives, although the latter do not absorb but only partially diffract or reflect UV light. Where other microparticles are added, the mixture may be further ground to provide a uniform mixture of microparticles..

In an embodiment particularly preferred for invisibility and lack of greasiness, the subject polymers may be readily formulated in combination with a carrier composition which comprises a tocopherol, including α-tocopherol, the tocopheryl esters, or any other functional analog or derivative thereof (for numerous well known tocopherol derivatives see, for example, U.S. Pat. Nos. 2,680,749, 5,686,632, 5,703,252 and 5,709,847), a mineral oil, a vegetable oil and/or a silicone oil. Most preferably, the carrier composition comprises a tocopherol or a functional analog or derivative thereof which provides for a sunscreen formulation that becomes invisible after application to the skin and is not oily. The amount of the tocopherol or analog or derivative thereof, vegetable oil or mineral oil added to the subject formulations may vary considerably to provide an acceptable formulation, wherein those amounts may be determined empirically in a routine manner. Optionally, the formulations may also comprise, for example, ascorbic acid (Vitamin C) or derivatives thereof, calendula oil, lanolin, coconut oil, petrolatum, silicone cosmetic wax, and/or oxides selected from the group consisting of zinc oxide or titanium oxide. Again, it is well within the skill level in the art to determine empirically the amount of each of these components to achieve an acceptable formulation.

The polymers of the subject invention will be present in the formulation in at least about 5 weight percent and not more than about 70 weight percent, usually ranging from about 10–50 weight percent. The dermatological formulation may be coated, sprayed, spread or otherwise applied to the particular surface, e.g., skin, as required and will be retained at the surface for extended periods of time. The formulations will be substantially invisible on the skin meaning that after application to the skin, the formulations will exhibit (or will eventually exhibit) a level of opacity that is not readily detected by the human eye.

The following examples are offered by way of illustration and not by way of limitation.

EXPERIMENTAL

EXAMPLE 1

Acrylamide of an Carboxy-Substituted Benzophenone 40 g (210 mmol) of 2-aminobenzophenone-2'-carboxylic acid were dissolved in 500 ml of EtOH and 111 ml of 9.5 N NaOH (1.05 moles). 100 ml of $H_2O$ were added, with stirring and cooling to 0–5° C., followed by 4.0 eq of acryloyl chloride. After completion and evaporation of EtOH, HCl was added to precipitate 2-acrylaminobenzophenone-2'-carboxylic acid (53 g, (86%), dry yield).

EXAMPLE 2

Acylation of 4-Amino Benzophenone with Acryloyl Chloride

4-Aminobenzophenone (10 g, 51 mmol, 1.00 eq) was dissolved in 40 ml of THF. After cooling to 5° C., acryloyl chloride (4.62 g, 51 mmol, 1.00 eq, in 10 ml THF) was added followed by triethylamine.

THF was removed, the oil dissolved in 100 ml of ethyl acetate and the organic layer extracted with 3×50 ml of $H_2O$. Ethyl acetate was removed to yield a solid of 10.5 g (82%).

EXAMPLE 3

N-acylation of p-Hydroxyaniline with p-Anisoyl Chloride p-Hydroxy aniline (152.6 g, 1.398 moles) was dissolved in 1.9 L tetrahydrofuran and 113 ml (110.6 g, 1.398 moles) pyridine. p-Anisoyl chloride (238.5 g, 1.398 moles) was added at 20° C. over 2.5 hours. After stirring for 2 hours, the solid was filtered and washed with THF. After reflux in 3 L methanol for 1.5 hours, filtering and washes with methanol, vacuum drying yielded a solid 262.8 g, (77%).

EXAMPLE 4

Acylation of 4-Methoxy-N-[1-(4-hydroxyphenyl)] Benzamide with Methacryloyl Chloride 4-Methoxy-N-[1-(4-hydroxyphenyl)] benzamide (200 g, 0.8221 moles) was dissolved in 650 ml dimethylacetamide and triethylamine (91.52 g, 0.9043 moles), cooled to –15° C., and methacryloyl chloride (94.53 g, 0.9043 moles) was added over an hour at –10° C. After warming to 20–25° C., the suspension was diluted with 650 ml acetonitrile. The solid was filtered, washed with acetonitrile and dried, then refluxed in 1.5 L methanol for 1.5 hours, cooled and filtered, washed with methanol, and vacuum dried to yield 177 g solid (69%).

EXAMPLE 5

Acylation of 4-Aminobenzoic Acid with Acryloyl Chloride

4-Aminobenzoic acid (10.00 g, 0.073 moles) was dissolved in a mixture of water (20 ml), ethanol (50 ml) and 5 N NaOH (37 ml). After cooling to 10° C., acryloyl chloride (8.58 g, 0.095 moles) was added with stirring, followed by 1 N NaOH (125 ml) and acryloyl chloride (8.58 g, 0.095 moles). Addition of 6 N HCl (25 ml) produced a suspension that was filtered, washed with water, dried resuspended in acetonitrile (200 ml) at 60° C., followed by filtration and drying to yield a solid 10.1 g (72%).

EXAMPLE 6

Amidation of 4-Acrylamidobenzoic Acid with Aniline

4-Acrylamidobenzoic acid (1.912 g, 10 mmol) was dissolved in 10 ml chloroform and triethylamine (1.113 g, 11 mmol). After cooling to –25° C., ethyl chloroformate (1.193 g, 11 mmoles) in 3 ml chloroform was added dropwise with stirring followed after 2 hours at –25° C., by aniline (0.931 g, 10 mmoles) in 2 ml acetonitrile. The reaction was stirred for 16 hours at room temperature, the solid was filtered, washed with chloroform, and dried, re-dissolved in ethyl acetate and isopentyl alcohol and extracted twice with bicarbonate. The organic layer was dried (MgSO$_4$), filtered, and evaporated to give a ytield of 1.30 g (50%).

EXAMPLE 7

Amidation of 4-Dimethylaminobenzoyl Chloride with Ethanolamine

4-Dimethylaminobenzoyl chloride (1.24 g, 6.75 mmoles) was dissolved in 15 ml THF and added to a stirred solution of ethanolamine (0.865 g, 14.17 mmoles) in 6 ml THF at −5° C. After 20 min at 20–25° C., THF was removed and the solids stirred with 15 ml water for 25 min. The solid was filtered, washed with water and vacuum dried to 1.13 g, then was crystallized from N-propanol yielding 0.92 g solid (65%).

EXAMPLE 8

Chlorination of 4-Dimethylaminobenzoic Acid

4-Dimethylaminobenzoic acid (250 g, 1.51 moles) was suspended in 2 L of ethyl acetate and thionyl chloride (359.3 g, 3.02 moles) was added. After the completion, the solvent was evaporated. Crystallization from ethyl acetate gave 216 g of 4-dimethylaminobenzoyl chloride (78%).

EXAMPLE 9

Acylation of 2-Hydroxyethyl Methacrylate with 4-Dimethylaminobenzoyl Chloride

4-Dimethylaminobenzoyl chloride (216 g, 1.18 moles) was suspended in 500 ml of ethyl acetate. 2-Hydroxyethyl methacrylate (169 g, 1.30 moles) was dissolved in 500 ml ethyl acetate and 165 ml triethylamine (119 g, 1.18 moles) and added to the acid while stirring. After the completion, more ethyl acetate was added and extracted with dilute sodium bicarbonate. Ethyl acetate was evaporated. Crystallization from ethanol gave 188.9 g (58%).

EXAMPLE 10

Esterification of 4-Hydroxydibenzoyl Methane with Methacryloyl Chloride

4-Hydroxydibenzoyl methane (1.97 g, 8.2 mmol) was dissolved in 15 ml of ethyl acetate and 1.25 ml of triethylamine (0.91 g, 8.98 mmol). Methacryloyl chloride (0.98 g, 9.4 mmol) was dissolved in 5 ml of ethyl acetate and added dropwise with stirring. Triethylamine hydrochloride was removed by extraction and ethyl acetate by evaporation. Crystallization from ethanol yielded 1.65 g of product (65%).

EXAMPLE 11

4-Tetrahydropyranyloxyacetophenone

4-Hydroxyacetophenone (75.00 g, 0.55 mol) was dissolved in ethyl acetate (300 ml) and a catalytic amount of methanesulfonic acid, and cooled to 0–4° C. Dihydropyran (204 ml, 2.20 moles, 4.0 eq) was slowly added. At room temperature, a white precipitate was formed, washed with water, and recrystallized from hexane. The yield was quantitative.

EXAMPLE 12

4-Hydroxydibenzoyl Methane

4-Tetrahydropyranloxyacetophenone (0.50 g, 2.11 mol) was dissolved in THF (6.0 ml). Sodium hydride (60% suspended in mineral oil, 170 mg, 4.23 mmol) was added. Methyl benzoate (0.53 ml, 4.23 mmol) was added and the mixture stirred at RT for 3 hours, then quenched with methanol. After solvent removal, the oil was dissolved in methylene chloride and washed with a 0.02 N aqueous solution of oxalic acid. The organic layer was then dried over anhydrous sodium sulfate. The product was dissolved in methanol (30 ml) and a 2 N aqueous solution of oxalic acid (10 ml) was added. After 2 hours at 42° C., a yellow solid was filtered off, dissolved in hot ethanol and precipitated by hexane to yield 0.456 g, 1.90 mmol (90%).

EXAMPLE 13

Acylation of 4-Hydroxydibenzoylmethane with Acryloyl Chloride

4-Hydroxydibenzoyl methane (10.00 g, 41.62 mmol) was dissolved in THF (25.0 ml). The solution was cooled to 0° C. and diazobicycloundecene (DBU) (7.50 ml, 50.00 mmol) was added at 0° C. followed by acryloyl chloride (5.92 ml, 72.84 mmol). After one hour, the reaction was quenched by methanol. After solvent removal, the crude oil was dissolved in dichloromethane/hexane. Silica gel (hexane/dichloromethane) column yielded a clear solid 5.60 g (46%).

EXAMPLE 14

Acylation of p-Hydroxymethacrylanilide with p-Anisoyl Chloride p-Hydroxymethacrylanilide (20.0 g, 113 mmol) was suspended in 250 ml ethyl acetate and 17.3 ml (12.6 g, 125 mmol) triethylamine. p-Anisoyl chloride (19.26 g, 113 mmol) was added at 25° C. over 15 minutes. After 24 hours at RT, the solid was filtered, washed with water (100 ml×3), then saturated bicarbonate solution (100 ml×3) and crystallized from methanol to give 27.1 g (77%).

EXAMPLE 15

Acylation of 2-Hydroxyethyl Methacrylate with p-Anisoyl Chloride

2-Hydroxyethyl methacrylate (5.00 g, 38.5 mmol) was dissolved in 25.0 ml ethyl acetate and triethylamine (4.25 g, 42.0 mmol). p-Anisoyl chloride (6.48 g, 38.5 mmol) was added at 5° C. over ten minutes. The reaction was stirred for 24 hours at RT. Triethylamine hydrochloride was filtered off and the filtrate washed with water (3×25.0 ml) and saturated bicarbonate solution (3×25.0 ml). The ethyl acetate layer was dried over MgSO$_4$, then stripped to a yellow oil which was distilled at 200° C. (0.1 mmHg) to yield 9.3 g, (91.3%).

EXAMPLE 16

Acylation of N-2-Hydroxyethyl Acrylamide with p-Anisoyl Chloride

N-2-hydroxyethyl acrylamide (5.00 g, 43.4 mmol) was dissolved in 35.0 ml ethyl acetate and triethylamine (4.83 g, 47.7 mmol). p-Anisoyl chloride (7.40 g, 43.4 mmol) was added at 5° C. over ten minutes. After 24 hours at RT, the solid was filtered and washed with water (3×25 ml), followed by saturated bicarbonate solution (3×25 ml), and drying to give a solid 9.36 g (93.6%).

EXAMPLE 17

Acylation of N-[2-Hydroxypropyl] Methacrylamide with 4-Dimethylaminobenzoyl Chloride 4-Dimethylaminobenzoyl chloride (56.21 g, 0.306 mol) was combined with N-[2-hydroxypropyl] methacrylamide (42.96 g, 0.30 mol) and 250 ml acetonitrile, stirred at RT and crystallized. After filtration, washing with cold acetonitrile and drying, 81.93 g (83.5%) was obtained.

80.00 g (0.2447 mol) of the HCl salt was suspended in 400 ml dichloromethane and sodium bicarbonate (21.00 g, 0.25 mol) in 300 ml water was added dropwise. The two phases were filtered and then separated. The $CH_2Cl_2$ layer was dried on $MgSO_4$, filtered, and evaporated to an oil that was crystallized from ethyl acetate to give 48 g of the free base.

EXAMPLE 18

Alkylation of Hydroxyethylmethacrylate with 4-Methoxycinnamyl Methanesulfonate 4-methoxycinnamyl alcohol (16.4 g, 100 mmol), prepared by reduction of the acid chloride using $NaBH_4$, $CeCl_3$ was dissolved in a mixture of $CH_2Cl_2$ (250 ml) and pyridine (25 ml) and cooled to 0–5° C. Methanesulfonyl chloride (9.28 ml, 120 mmol) was added and the reaction stirred for 6 hours at 20° C. The product was filtered and purified on silica gel.

4-methoxycinnmyl methanesulfonate (15 g, 65 mmol) was dissolved in THF (100 ml) and added to a cold solution of 2-hydroxyethyl methacrylate (16.83 g, 130 mmol), BHT (20 mg), THF (50 ml) and lithiun bis-(trimethyl silyl)amide (1M solution in THF, 100 ml, 100 mmol), allowed to stir for 12 hours at 20° C. and poured into a mixture of EtOAc, 1 N HCl and cold water. After separation, the organic layer was washed with saturated NaCl (100 ml), dried with $MgSO_4$ and evaporated.

EXAMPLE 19

Acylation of Hydroxypropyl Methacrylate with 4-Methoxycinnamic Acid 4-methoxycinnamic acid chloride (19.65 g, 100 mmol) was dissolved in $CH_2Cl_2$ (100 ml) and added to a cold solution of hydroxypropyl methacrylate (15.9 g, 110 mmol), triethylamine (16.73 ml, 120 mmol) and $CH_2Cl_2$ (100 ml). After stirring for 12 hours at 20° C., the reaction mixture was poured into cold water. The layers were separated and the organic layer washed with saturated $NaHCO_3$ (50 ml) and saturated NaCl (2×50 ml). After drying ($MgSO_4$) and stripping, the product was isolated as a yellow oil.

EXAMPLE 20

Polymerization of a UV-A Monomer, a UV-B Monomer, and a UV-C Monomer

A 1 liter flask was charged with 30.83 g (0.1 moles) UV-A monomer 4-methacryloxydibenzoyl methane, 29.04 g (0.1 moles) UV-B monomer N-[2-(4'-dimethylaminobenzoyl) oxypropyl] methacrylamide, 31.13 g (0.1 moles) UV-C monomer 4-methoxy-N-[1-(4-methacryloxyphenyl)] benzamide, 9.76 g (0.075 moles) 2-hydroxyethylmethacrylate, 1.73 g (0.01125 moles) N,N-methylene bisacrylamide, and 500 ml methanol. After flushing with argon, 0.951 g (0.00579 moles) of 2,2'-azobis butyronitrile was added along with 250 ml of MeOH. After stirring at 60° C. for 20 hours the sunscreen polymer was filtered, washed with methanol, and vacuum dried to a mass of 90.66 g.

EXAMPLE 21

Preparation of a UV-A and UV-B Absorbing Polymer with Low HEMA Content

A 2 L flask was charged with 50 g (0.172 moles) of UV-B monomer N-[2-(4'-dimethylaminobenzoyl)oxy] propyl methacrylamide, and the commercially obtained UV-A monomer 2-(2'-hydroxy-5-methacryloxy ethyl phenyl)-2H-benzotriazole, 20 g (0.062 moles), 25 g (0.192 moles) of 2-hydroxyethylmethacrylate, 4 g (0.026 moles) N,N-methylene bisacrylamide and 1 L methanol. After flushing with argon, 1 g (0.0061 moles) of 2,2'-azobisisobutyronitrile was added to the flask. After stirring at 60° C. for 48 hours, the formed polymer was filtered, washed with methanol, vacuum dried to a mass of 93.4 g, and then washed with isopropanol (2×100 ml), filtered and dried at 60° C. to give an analytically uniform product of 89.4 g, which was ground in the ball-grinder for 120 minutes to produce a powder with particles in the range of 1 micron.

EXAMPLE 22

Preparation of a UV-A Absorbing Polymer with Low HEMA Content

A 2 L flask was charged with 100 g (0.309 moles) of the commercially obtained UV-A monomer 2-(2'-hydroxy-5'-[2"-methacryloxyethyl]phenyl)-2H-benzotriazole, 32.96 g (0.253 moles) of 2-hydroxyethyl methacrylate, 0.56 g (0.0028 moles) ethylene glycol dimethacrylate and 1 L methanol. After flushing with argon, 1.4 g (0.0085 moles) of 2,2'-azobisisobutyronitrile was added to the flask. After stirring at 60° C. for 48 hours, the formed polymer was filtered, washed with methanol, vacuum dried to a mass of 122.8 g, and then washed with isopropanol (2×100 ml), filtered and dried at 60° C. to give an analytically uniform product of 116.7 g, which was ground in a ball-grinder for 120 minutes to produce a powder with particles in the range of 1 micron.

EXAMPLE 23

Preparation of a UV-A and UV-B Absorbing Polymer with Low HEMA Content

A 2 L flask was charged with 52.35 g (0.172 moles) 2-propenoic acid, 2-methyl-, 3-[[3-(4-methoxy phenyl)-1-oxo-2-propenyl]oxy]propyl ester, and the commercially obtained UV-A monomer 2-(2'-hydroxy-5'-[2"-methacryloxyethyl]phenyl)-2H-benzotriazole, 20 g (0.062 moles), 25 g (0.192 moles) of 2-hydroxyethyl methacrylate, 5.15 g (0.0026 moles) ethylene glycol dimethacrylate and 1 L methanol. After flushing with argon, 1 g (0.0061 moles) of 2-2'-azobisisobutyronitrile was added to the flask. After stirring at 60° C. to give an analytically uniform product of 89.8 g, which was ground in a ball-grinder for 120 minutes to produce a powder with particles in the range of 1 micron.

EXAMPLE 24

Preparation of a UV-A and UV-B Absorbing Polymer with Low HEMA Content

A 2 L flask was charged with 47.18 g (0.172 moles) of UV-B monomer 2-propenoic acid, 2-methyl-, 2-[[3-(4-methyoxy phenyl)-2-propenyl]oxy] ethyl ether, and the commercially obtained UV-A monomer 2-(2'-hydroxy-5'-[2"-methacryloxyethyl]phenyl)-2H-benzotriazole, 20 g (0.062 moles), 25 g (0.192 moles) of 2-hydroxyethyl methacrylate, 5.15 g (0.0026 moles) ethyleneglycol dimethacrylate and 1 L methanol. After flushing with argon, 1 g (0.0061 moles) of 2,2'-azobisisobutyronitrile was added to the flask. After stirring at 60° C. to give an analytically uniform product of 89.8 g, the product was ground in a ball-grinder for 120 minutes to produce a powder with particles in the range of 1 micron.

EXAMPLE 24

Polymerization of UV-A and UV-B Absorbing Monomers with HEMA 10.5 g (0.0340 moles) of 4-(3'-oxo-3'-phenylpropanoyl) phenyl 2"-methylprop-2"-enoate was suspended with 10.5 g ((0.03616 moles) of 2-(3-[4-methoxyphenyl]prop-2-enoylamino) 2-methylprop-2-enoate. 0.150 g (0.75 mmoles) of ethylene glycol dimethacrylate and 7.5 g (0.05763 moles) 2-hydroxyethyl methacrylate and 300 mL of toluene. After flushing with nitrogen, 0.3 g of 2,2'-azo-bis-isobutyronitrile was added. After stirring at 65° C. for 48 h, a fine particle solid was filtered, washed with isopropyl alcohol and vacuum dried to yield 25.41 g (84.7%).

EXAMPLE 25

Polymerization of UV-A Absorbing Polymer with HEMA 28 g (0.091 moles) of 4-(3'-oxo-3'-phenylpropanoyl) phenyl 2"-methylprop-2"-enoate, 11.4 g (0.088 moles) of 2-hydroxyethyl methacrylate, 0.2 g (1 mmole) ethylene glycol dimethacrylate and 0.4 L of toluene was combined. After flushing with nitrogen, 0.4 g (2.4 mmoles) of 2.,2'-azobisisobutyronitrile was added. After stirring at 60° C. for 48 h, a fine particulate solid was filtered, washed with isopropanol and vacum dried to yield 34.52 g (86.3%).

EXAMPLE 25

Formulation of a Sunscreen Cream

Into a ball-grinder 1.38 grams of lanolin, 300 mg of Vitamin E acetate, 1.476 g of copra oil, 180 mg of silicone wax (Dow Corning 2503) and 180 mg of white petrolatum were added together with 2.4 g of the polymer prepared as described in Example 20 above and 120 mg of titanium dioxide. All ingredients were mixed and groud at room termperature for 90 minutes to produce a cream. When applied to the skin, the cream film takes a grayish-white color which becomes transparent over about 15 to 20 minutes. Since the particles are in the range of 1 micron in size, transfer into the skin and underlying strata is prevented.

EXAMPLE 26

Formulation of a Sunscreen Cream

Into a ball-grinder 1.38 grams of lanolin, 300 mg of Vitamin E acetate, 1.476 g of copra oil, 180 mg of silicone wax (Dow Corning 2503) and 180 mg of white petrolatum were added together with 1.24 g of the polymer prepared as described in Example 22, 1.2 g of the commerically available octyl methoxycinnamate, and 120 mg of titanium dioxide. All ingredients were mixed and groud at room termperature for 90 minutes to produce a cream. When applied to the skin, the cream film takes a grayish-white color which becomes transparent over about 15 to 20 minutes. Since the particles are in the range of 1 micron in size, transfer into the skin and underlying strata is prevented.

In accordance with the invention, novel compositions are provided which give skin protection from erythema, carcinogenicity and other deleterious effects of ultraviolet radiation, while being biologically inert and invisible. The compositions have good retentive capability, provide a smooth coating on the skin, and do not penetrate into the dermal layer, where the currently used aromatic light absorbing moieties could have adverse effects. At the same time, unlike the biologically inert zinc or titanium oxides, at the cost of a white ot violet tinge, the novel compositions are both inert and invisible. The compositions may be readily prepared from readily available compounds in accordance with conventional ways. For eye lenses, novel compositions are purified which are biologically and optically integral covalent parts of the lens to protect the eve from UV radiation, while the compositions are also biologically inert.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A sunscreen formulation comprising:

an effective amount for absorbing ultraviolet sunlight of a polyacrylic acid sunscreen composition comprising in combination at least two UV absorbing moieties covering the UV-A and UV-B ranges and comprising at least one of an unsubstituted acrylic acid or substituted acrylic acid comprising a side chain having at least one oxy group covalently bonded to said polyacrylic acid through an oxygen or nitrogen atom, wherein the number ratio of the total of said UV absorbing moieties to said side chain and unsubstituted acrylic acid groups is in the range of 0.1–10:1, said polyacrylic acid sunscreen composition forming substantially insoluble particles, and a carrier composition comprising one or more of a tocopherol or a functional analog or derivative thereof, a vegetable oil, a mineral oil or a silicone oil which is capable of being absorbed by said polyacrylic acid sunscreen compositon to alter its refractive index and render said formulation substantially transparent on the skin.

2. The sunscreen formulation according to claim 1, wherein said carrier composition comprises a tocopherol or a functional analog or derivative thereof.

3. The sunscreen formulation according to claim 1, wherein said carrier composition comprises a tocopherol.

4. The sunscreen formulation according to claim 1, further comprising ascorbic acid or a derivative thereof.

5. The sunscreen formulation according to claim 1, further comprising one or more of lanolin, coconut oil, calendula oil, petrolatum and silicone wax.

6. The sunscreen formulation according to claim 1, further comprising an oxide selected from the group consisting of zinc oxide and titanium oxide.

7. The sunscreen formulation according to claim 6, wherein said formulation contains 1 to 4% of said oxide.

8. A sunscreen formulation comprising an effective amount for absorbing ultraviolet sunlight of a polyacrylic sunscreen having as UV absorbing moieties:

(1) for UV-A, a compound of the formula:

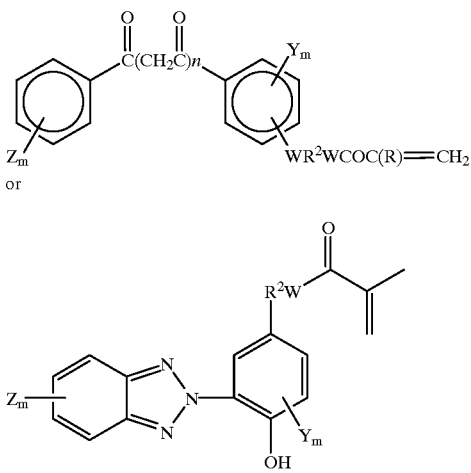

or wherein:
n is 0 or 1;
m is 0, 1, 2 or 3;
R is H, alkyl of from 1 to 3 carbon atoms, which may be substituted with a functional group of from 0 to 3 carbon atoms having from 1 to 2 nitrogen and oxygen heteroatoms;
$R^2$ is a bond or hydrocarbylene or substituted hydrocarbylene of from 1 to 8 carbon atoms, with the proviso that when $R^2$ is a bond or only one carbon atom, only one W is present;
Z is oxy or amino substituted by not more than about 12 carbon atoms or R;
Y is non-oxo carbonyl substituted by not more than about 12 carbon atoms or R; and
W is oxy or amino;

(2) for UV-B, a compound of the formula:

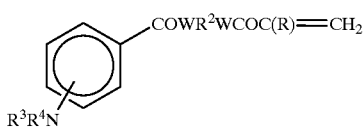

wherein:
$R^3$ and $R^4$ are hydrogen or alkyl of up to 6 carbon atoms and are the same or different;
W, R and $R^2$ are as defined above; or

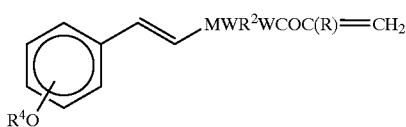

wherein:
M is carbonyl or methylene;
W, R, $R^2$ and $R^4$ are as defined above; and (3) and optionally for any UV-C, a compound of the formula:

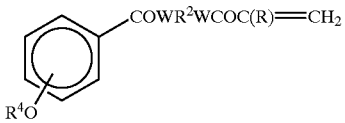

wherein:
$R^4$ is hydrogen or alkyl of from 1 to 6 carbon atoms; and
the other symbols have been defined above; and
a carrier composition comprising one or more of a tocopherol or a functional analog or derivative thereof, a vegetable oil, a mineral oil or a silicone oil.

9. The sunscreen formulation according to claim 8, wherein said carrier composition comprises a tocopherol or a functional analog or derivative thereof.

10. The sunscreen formulation according to claim 8, wherein said carrier composition comprises a tocopherol.

11. The sunscreen formulation according to claim 8, further comprising ascorbic acid or derivative thereof.

12. The sunscreen formulation according to claim 8, further comprising one or more of lanolin, coconut oil, calendula oil, petrolatum and silicone wax.

13. The sunscreen formulation according to claim 8, further comprising an oxide selected from the group consisting of zinc oxide and titanium oxide.

14. The sunscreen formulation according to claim 13, wherein said formulation contains 1 to 4% of said oxide.

15. The sunscreen formulation according to claim 8, wherein the UV-B absorbing moiety is a cinnamate.

16. The sunscreen formulation according to claim 15 which is selected from the group consisting of (a) 3-(3-(4-methoxyphenyl)prop-2-enoyloxy)propyl 2-methylprop-2-enoate, (b) 2-(3-(4-methoxyphenyl)prop-2-enoyloxy)-isopropyl 2-methylprop-2-enoate and (c) 2-(3-(4-methoxyphenyl)prop-2-enoyloxy)propyl 2-methylprop-2-enoate.

17. The sunscreen formulation according to claim 8, wherein the UV-B absorbing moiety is a reduced cinnamate.

18. The sunscreen formulation according to claim 17 which is selected from the group consisting of (a) 3-(3-(4-methoxyphenyl)prop-2-enyloxy)propyl 2-methylprop-2-enoate, (b) 2-(3-(4-methoxyphenyl)prop-2-enyloxy)-isopropyl 2-methylprop-2-enoate, (c) 2-(3-(4-methoxyphenyl)prop-2-enyloxy)propyl 2-methylprop-2-enoate and (d) 2-3-(4-methoxyphenyl)prop-2-enyloxy)ethyl 2-methylprop-2-enoate.

19. The sunscreen formulation according to claim 8, wherein the UV-A absorbing moiety is 2-(2'-hydroxy-5-methyacryloxyethylphenyl)-2H-benzotriazole.

20. A method for preparing a suncreen formulation, said method comprising the step of:
combining (a) an effective amount for absorbing ultraviolet sunlight of a polyacrylic acid sunscreen composition comprising in combination at least two UV absorbing moieties covering the UV-A and UV-B ranges and comprising at least one of an unsubstituted acrylic acid or substituted acrylic acid comprising a side chain having at least one oxy group covalently bonded to said polyacrylic acid through an oxygen or nitrogen atom, wherein the number ratio of the total of said UV absorbing moieties to said side chain and unsubstituted acrylic acid groups is in the range of 0.2–10:1 with (b) a carrier composition comprising one or more of a tocopherol or a functional analog or derivative thereof, a vegetable oil, a mineral oil or a silicone oil, said combining providing said sunscreen formulation.

21. A method for preparing a sunscreen formulation, said method comprising the step of:

combining (a) an effective amount for absorbing ultraviolet sunlight of a polyacrylic sunscreen having as UV absorbing moieties:

(1) for UV-A, a compound of the formula:

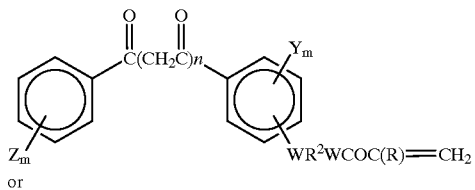

or

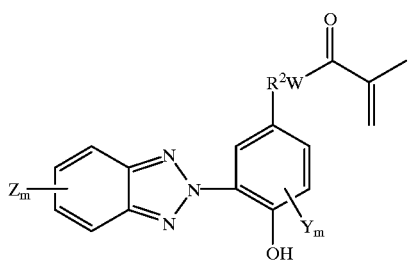

wherein:

n is 0 or 1;

m is 0, 1, 2 or 3;

R is H, alkyl of from 1 to 3 carbon atoms, which may be substituted with a functional group of from 0 to 3 carbon atoms having from 1 to 2 nitrogen and oxygen heteroatoms;

$R^2$ is a bond or hydrocarbylene or substituted hydrocarbylene of from 1 to 8 carbon atoms, with the proviso that when $R^2$ is a bond or of one carbon atom, only one W is present;

Z is oxy or amino substituted by not more than about 12 carbon atoms or R;

Y is non-oxo carbonyl substituted by not more than about 12 carbon atoms or R; and W is oxy or amino;

(2) for UV-B, a compound of the formula:

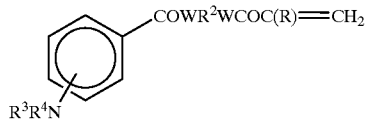

wherein:

$R^3$ and $R^4$ are hydrogen or alkyl of up to 6 carbon atoms and are the same or different;

W, R and $R^2$ are as defined above; or

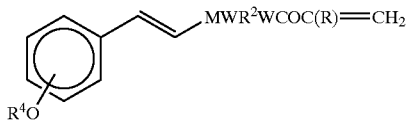

wherein:

M is carbonyl or methylene;

W, R, $R^2$ and $R^4$ are as defined above; and (3) optionally for any UV-C, a compound of the formula:

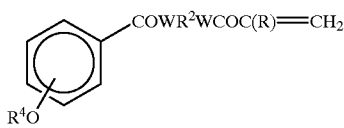

wherein:

$R^4$ is hydrogen or alkyl of from 1 to 6 carbon atoms; and the other symbols have been defined above, with (b) a carrier composition comprising one or more of a tocopherol or a functional analog or derivative thereof a vegetable oil, a mineral oil or a silicone oil, wherein said step of combining provides said sunscreen formulation.

22. A sunscreen formulation comprising:

an effective amount for absorbing ultraviolet sunlight of a polyacrylic acid sunscreen composition comprising in combination a UV-A absorbing moiety, 4-(3'-oxo-3'-phenylpropanoyl)phenyl 2"-methylprop-2"-enoate, and 2-hydroxyethyl methacrylate, wherein the number ratio of the total of said UV-A absorbing moiety to said 2-hydroxyethyl methacrylate is in the range of 0.1–10:1, said polyacrylic acid sunscreen composition forming substantially insoluble particles, and a carrier composition comprising one or more of a tocopherol or a functional analog or derivative thereof, a vegetable oil, a mineral oil or a silicone oil which is capable of being absorbed by said polyacrylic acid sunscreen compositon to alter its refractive index and render said formulation substantially transparent on the skin.

* * * * *